(12) United States Patent
Nakatsuka et al.

(10) Patent No.: US 8,662,350 B2
(45) Date of Patent: Mar. 4, 2014

(54) STORAGE CONTAINER FOR DENTAL ADHESIVE

(75) Inventors: Toshiyuki Nakatsuka, Kyoto (JP);
Yusei Kadobayashi, Kyoto (JP);
Masaru Ito, Toyama (JP)

(73) Assignee: Shofu Inc., Kyoto (JP)

( * ) Notice: Subject to any disclaimer, the term of this patent is extended or adjusted under 35 U.S.C. 154(b) by 555 days.

(21) Appl. No.: 12/550,408

(22) Filed: Aug. 31, 2009

(65) Prior Publication Data
US 2010/0075276 A1    Mar. 25, 2010

(30) Foreign Application Priority Data
Sep. 19, 2008  (JP) .................................. 2008-241422

(51) Int. Cl.
*B65D 35/56*   (2006.01)

(52) U.S. Cl.
USPC ............ 222/105; 222/107; 222/131; 222/183

(58) Field of Classification Search
USPC ................. 222/92–107, 131, 183, 209, 215
See application file for complete search history.

(56) References Cited

U.S. PATENT DOCUMENTS

| | | | | |
|---|---|---|---|---|
| 3,643,837 A | * | 2/1972 | Green ............................ | 222/101 |
| 4,421,251 A | * | 12/1983 | Namdari et al. ................ | 222/99 |
| 5,529,217 A | * | 6/1996 | Siegel ............................ | 222/131 |
| 5,653,360 A | * | 8/1997 | Brandhorst et al. ............ | 222/95 |
| 5,833,119 A | * | 11/1998 | Kolacek .......................... | 222/41 |
| 2009/0001098 A1 | * | 1/2009 | Chen .............................. | 222/107 |

FOREIGN PATENT DOCUMENTS

| | | |
|---|---|---|
| JP | 1990-143916 U | 12/1990 |
| JP | 1994-044779 U | 6/1994 |
| JP | 10-175683 | 6/1998 |
| JP | 2002-513665 A | 5/2002 |

* cited by examiner

*Primary Examiner* — Paul R Durand
*Assistant Examiner* — Andrew P Bainbridge
(74) *Attorney, Agent, or Firm* — Lee Fredric Sharra (57) ABSTRACT

There is provided a storage container for a dental adhesive that allows a stable dropping operation during use of a dental adhesive and smooth fine dropping work such as strict control of an amount of drops with high reproducibility, and can prevent expansion of an adhesive stored in the storage container caused by a temperature increase. A storage container for a dental adhesive is used, including a cylindrical container portion that can store a liquid such as an adhesive therein, wherein one end surface of the container portion has a discharge port communicating with an outside, the other end surface of the container portion is closed by a bottom wall, and a tail portion is formed protruding from the bottom wall to the side opposite from the discharge port.

8 Claims, 6 Drawing Sheets

21 OUTER CONTAINER (13 TAIL PORTION)

21 OUTER CONTAINER (13 TAIL PORTION)

STORAGE CONTAINER FOR DENTAL ADHESIVE

BACKGROUND OF THE INVENTION

1. Field of the Invention

The present invention relates to a storage container for a dental adhesive used for treatment of dental caries in dentistry.

2. Description of the Related Art

"Tooth decay" generally called dental caries is a common disease in dentistry, and many people experience tooth decay regardless of age or sex. When tooth decay advances, the tooth decay does not naturally heal but needs to be treated by a dentist. A widely used method for the treatment is to shave a tooth decay portion down with a dental grinding tool to form a cavity, fill a dental restoratives such as composite resin into the cavity, and reproduce natural tooth anatomy. The composite resin is mainly classified into chemical polymerization resin and photo polymerization resin by a difference in curing method, and these resins are used for different applications.

The composite resin cannot adhere to teeth substance by itself, and requires a dental adhesive applied between the composite resin and the teeth substance. In recent years, technical developments in the field of dental adhesives have been rapidly made, and firm adhesion to adherend such as metal, ceramic, or composite resin has been achieved in addition to firm adhesion to the teeth substance. Conventionally, a plurality of steps such as etching, priming, and bonding are required during use of an adhesive. Liquid materials such as adhesives stored in storage containers for the respective steps are dropped onto different wells on a dish, and applied to an application site in order according to a procedure. However, driven by users' needs for a simplified operation procedure and a stable adhesive property, a self-etching primer used in a combined step of etching and priming, and an all-in-one adhesive used in a combined step of etching, priming, and bonding have been developed to improve operability and an adhesive property and reduce the number of storage containers for storing liquid materials. However, the all-in-one adhesive or the like does not totally replace, but a two liquid mixing type adhesive used by dropping desired amounts of liquid materials from two storage containers in order onto the same well on a dish so as to contact with each other and mixing the liquid materials has been also widely used.

A trace amount of dental adhesive is applied at one time, and thus too large an amount of drops from a storage container increase an amount of waste and thus increase cost. Thus, to reliably control a trace amount of drops, a shape or a diameter of a discharge port of a nozzle located at a distal end of the container, and a length and a hole diameter of a channel connecting to the nozzle are strictly controlled. Particularly, more strict control is performed for achieving designed performance with a two liquid mixing type adhesive because amounts of drops of adhesives and a mixing ratio thereof are important. Since a trace amount of adhesive is applied at one time as described above and also there is an expiration date, a storage container for the adhesive is naturally small, and a height from a bottom to a cap is 5 cm maximum. Thus, to drop the adhesive onto a dish, the storage container is generally turned downward and pressed at side surfaces by a thumb and an index finger holding the side surfaces. This pressing operation is generally called "squeeze".

SUMMARY OF THE INVENTION

As described above, technical developments of adhesives have been rapidly made, and composition of adhesives has been changed. The composition of adhesives has been shifting to low viscosity composition including water or a volatile solvent as a main ingredient for increased wettability or permeability to an application site and reliable drying after application. Thus, with the conventional dropping manner to press the side surfaces of the container with the thumb and the index finger, surface tension of an adhesive is low, and the adhesive may flow out by itself and naturally drops onto a place other than the dish when the storage container is tilted. Also, when the storage container is pressed, an error in an amount of drops beyond an acceptable range may occur according to a slight difference in a level of force. As such, the conventional dropping manner does not match the actual situation with the shifting composition of adhesives, and is unsuitable for fine dropping work due to insufficient stability of a dropping operation and an amount of drops.

Also, a position of the storage container during squeeze differs depending on dentists' preferences. For example, the nozzle is turned substantially downward or turned substantially horizontally. Such a change in the position changes a positional relationship between a liquid level in the container and a discharge port. This causes variations in the amount of drops, leading to a case where the adhesive is dropped more than necessary. For the two liquid mixing type adhesive, an accurate mixing ratio cannot be maintained.

Further, a dental adhesive needs to be stored in a refrigerator to maintain its quality. The adhesive is left at room temperature before use, and actually used after reaching room temperature. When a storage container thus taken out of the refrigerator is handled, body heat from fingers is transferred via the storage container to the adhesive. Thus, a volatile solvent contained in the adhesive may expand, and a phenomenon unexpected to a user may occur such that the adhesive spouts from a distal end of a nozzle when a cap is removed, or the adhesive continuously drops from the distal end of the nozzle during dropping. A technique as disclosed in Japanese Patent No. 3572158 has been developed to prevent a temperature increase by heat transfer from fingers in such a dropping operation process. The technique relates to a container having a double structure, and an air layer is formed between an outer container and an inner container to prevent heat transfer from fingers, thereby preventing expansion of an adhesive stored in a storage container caused by a temperature change.

The present invention is achieved in view of such circumstances, and has an object to provide a storage container for a dental adhesive that allows a stable dropping operation during use of a dental adhesive and smooth fine dropping work such as strict control of an amount of drops with high reproducibility, and can prevent expansion of an adhesive stored in the storage container caused by a temperature increase.

To solve the above described problems, the invention according to claim 1 provides a storage container for a dental adhesive, including an elongated container portion that can store a liquid therein, wherein one end surface of the container portion has a discharge port communicating with an outside, the other end surface of the container portion is closed by a bottom wall, and a tail portion is formed protruding from the bottom wall to the side opposite from the discharge port.

The storage container according to the present invention is intended for supplying a dental adhesive to a dentist or the like, and is not used in a production stage. The container portion as a component of the storage container is a hollow portion for storing various liquids used in a series of adhesive steps such as etching, priming, and bonding, and has an elongated cylindrical shape with reliable sealability, but may have any sectional shape such as a circular shape or a square or hexagonal shape. The discharge port has a function of discharging the liquid stored in the container portion to the outside, and is provided in the one end surface of the container portion. The discharge port does not always need to be integrally formed with the container portion, but may be incorporated into the container portion using a plug having a discharge port. Both cases require a separate removable cap for closing the discharge port.

The one end surface of the container portion thus has the discharge port, and the opposite side has the bottom wall for sealing the inside of the container portion. In the present invention, the tail portion is formed protruding from the bottom wall to the side opposite from the discharge port. The tail portion may be integrally formed with the container portion, or may be separately fabricated and joined to the container portion. The tail portion preferably has an integrated shape without a step or the like at a boundary between the tail portion and the container portion, and may further have a tapered end for good appearance. The tail portion merely protrudes from the bottom wall of the container portion, and cannot store the liquid therein. Forming the tail portion can increase an entire length of the storage container without increasing the content, and allows the container to be supported by a thumb and an index finger and also by a side of a middle finger and a base of the index finger like a writing instrument such as a pencil during use, thereby increasing stability. In the present invention, the container portion, the discharge port, and the tail portion are all made of resin, but a detailed material is not limited.

In the invention according to claim 2, a shape of the storage container is limited, and a length between the discharge port and an end surface of the tail portion is 8 to 15 cm. This length refers to a linear distance between a distal end of the discharge port and a rear end surface of the tail portion with the cap being removed. The length is thus limited, and the tail portion comes into contact with the base of the index finger when a portion near the discharge port is held by the thumb and the index finger, thereby increasing stability. Also, the length is not too long, thereby providing easy handling and high operability. With a length of less than 8 cm, the tail portion does not come into contact with the base of the index finger in some cases, thereby preventing convenience offered by the present invention from being obtained.

In the invention according to claim 3, an outer container surrounding an outer periphery of the container portion is further provided, and the tail portion is formed to extend in a longitudinal direction of the outer container. The outer container surrounds the outside of the container portion, and in the present invention, the outer container is formed to extend in the longitudinal direction so as to have a function of the tail portion. Thus, the outer container according to the present invention is longer than the container portion, and protrudes rearward beyond the bottom wall. The outer container also functions as a heat insulating material for reducing temperature changes of the liquid stored in the container portion. It is not always necessary to ensure an air layer between the container portion and the outer container, but the both may entirely come into contact with each other. However, it is necessary that pressing the outer container deforms the container portion to allow the liquid therein to be reliably dropped.

In the invention according to claim 4, the shape of the outer container is limited, and a slit is formed in the longitudinal direction in a side surface of the outer container. The slit is formed by cutting the side surface of the outer container in the longitudinal direction, and with one line of slit, the outer container has a C-shaped cross section. Thus, when the side surface of the outer container is pressed, the outer container is easily deformed so as to reduce an inner diameter thereof, thereby allowing the container portion in contact with the inside of the outer container to be easily pressed, and allowing the liquid to be smoothly discharged. Particularly, when a thickness of the outer container is increased for increasing a heat insulating property or gripping feeling, rigidity of the outer container is necessarily increased to provide a noticeable advantage of the slit.

The slit is basically formed in the longitudinal direction of the storage container, but may be slightly oblique. The slit is formed to connect both end surfaces of the outer container so that the entire outer container has a C-shaped section. Alternatively, the slit may be formed in a region only overlapping the container portion, and a remaining region may have no slit so that the outer container in the remaining region has an annular section. When the slit is thus formed in a limited region, two or more lines of slits may be formed, thereby further increasing flexibility.

As in the invention according to claim 1, the tail portion protruding to the side opposite from the discharge port is provided in addition to the container portion for storing the liquid such as the adhesive. Thus, the portion near the discharge port can be supported by the thumb and the index finger, and also the tail portion of the storage container can be supported by the base of the index finger during use. Thus, the storage container of the present invention can be held at three or more points like when a writing instrument such as a pencil is held, thereby providing high stability of a holding state during a dropping operation. This stabilizes squeeze during dropping, thereby allowing a minimum necessary amount of liquid to be accurately and quickly dropped, allowing a minimum amount of liquid to remain on a dish after treatment, and reducing cost.

The position of the conventional storage container during use differs depending on dentists' preferences, and this causes variations in the amount of drops. In the present invention, the storage container is naturally fixedly held like when a writing instrument is held, and this always provides a stable position and a constant amount of drops. Also, the operation can be performed in a natural position like when a writing instrument is handled, thereby achieving a smooth and quick dropping operation, and preventing a temperature increase of the liquid in the storage container caused by heat transfer. Further, a two liquid mixing type adhesive requires an accurate and strict amount of drops for achieving an original adhesive property. In the present invention, as described above, the adhesive can be quickly and smoothly dropped with the same feeling as when a writing instrument is handled, a mixing ratio of liquids to be dropped can be accurately controlled, a predetermined adhesive property can be achieved, and a working time can be reduced. The tail portion in the present invention does not have a function of storing the adhesive, and thus the content and control of an expiration date are the same as in the conventional storage container.

As in the invention according to claim 2, the entire length of the storage container is limited, and the portion near the discharge port of the storage container is held by the thumb and the index finger during use, the tail portion of the storage container naturally comes into contact with the base of the index finger, thereby reliably providing the advantage of the invention in claim 1. Also, the length is not too long, thereby providing high operability and easy storage.

As in the invention according to claim 3, the outer container is provided separately from the container portion for storing the liquid, and the one end of the outer container is protruded to form the tail portion. This achieves the same operability as a writing instrument as in the invention according to claim 1. Also, the double structure including the container portion and the outer container increases a heat insulating property, thereby preventing rapid expansion of a volatile liquid, and preventing the liquid from dropping in an unexpected situation. As in the invention according to claim 4, the slit is provided in the outer container to reduce rigidity of the outer container, and thus light pressing of the outer container allows a desired amount of liquid to be dropped.

BRIEF DESCRIPTION OF THE DRAWINGS

FIGS. 1A and 1B show a shape example of a storage container according to the present invention.

FIGS. 2A, 2B, 2C and 2D show details of the storage container in FIG. 1.

FIGS. 3A, 3B, 3C and 3D show a storage container having a different structure from the storage container in FIG. 1.

FIGS. 4A and 4B are vertical sectional views of storage containers including a container portion and a tail portion integrally formed unlike the storage container in FIG. 1 or the like, FIG. 4A shows a storage container with a hollow tail portion, and FIG. 4B shows a storage container with a solid tail portion;

FIGS. 5A, 5B, 5C and 5D show a shape example of a storage container.

DETAILED DESCRIPTION OF THE PREFERRED EMBODIMENTS

Figure 1:
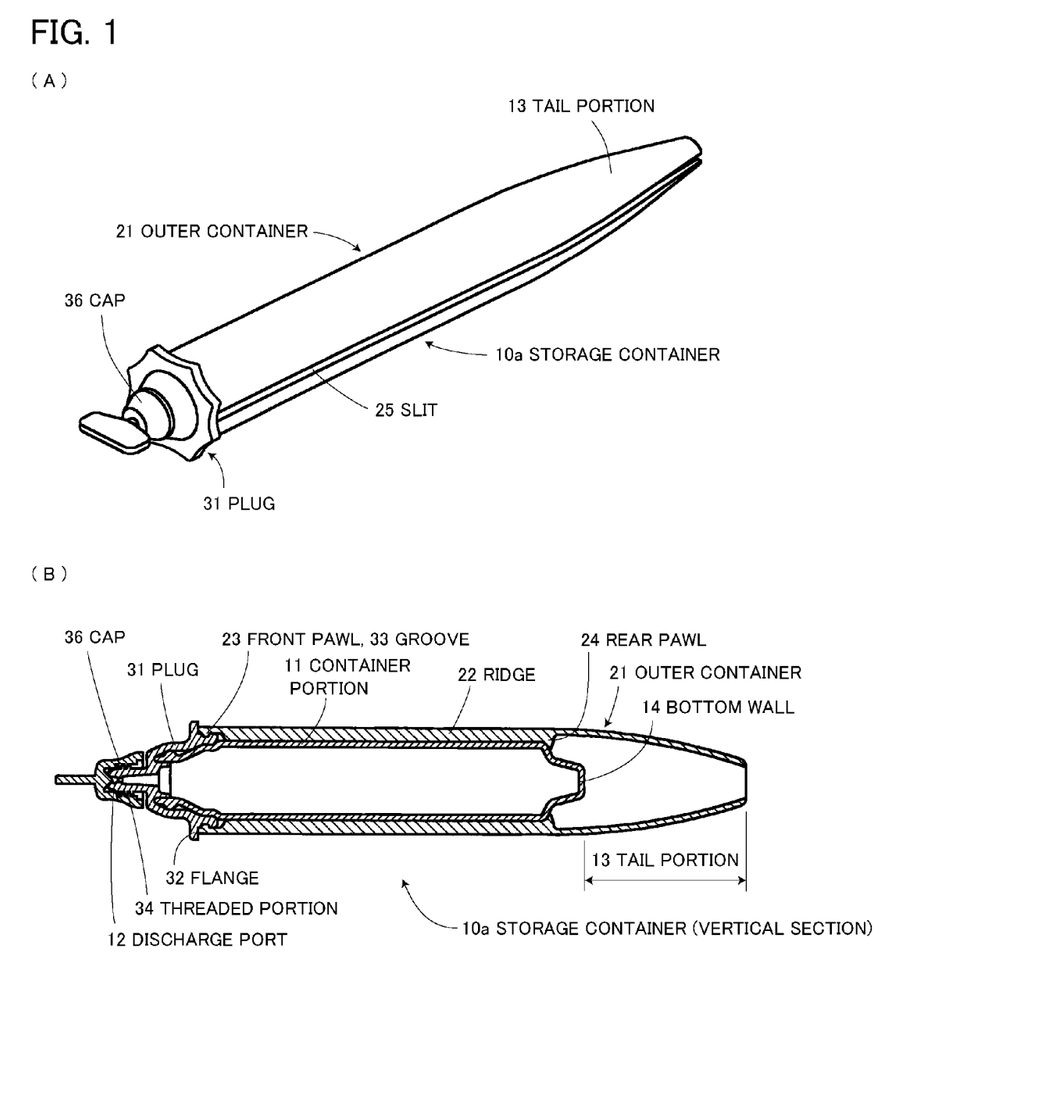
FIG. 1A is a perspective view of an appearance.
FIG. 1B is a vertical sectional view of a central portion.

FIG. 1 shows a shape example of a storage container 10a according to the present invention, FIG. 1A shows an appearance, and FIG. 1B is a vertical sectional view of a central portion. The storage container 10a according to the present invention is in the shape of a rod having a substantially circular section, and includes therein a container portion 11 for storing various liquids used in a series of adhesive steps such as etching, priming, and bonding, and a discharge port 12 for dropping the liquids in a left end surface in FIG. 1. A side peripheral surface of the container portion 11 is covered with an outer container 21, and a right end of the outer container 21 is tapered into a conical shape. The discharge port 12 is formed in a distal end of a plug 31 produced separately from the container portion 11, and a cap 36 is threaded on the plug 31 to seal the inside of discharge port 12. Thus, threaded portions 34 are formed on an outer periphery of the plug 31 and an inner periphery of the cap 36. The container portion 11 and the outer container 21 are made of relatively soft polypropylene resin, and the plug 31 and the cap 36 are made of harder polyethylene terephthalate resin for ensuring sealability.

The container portion 11 has a simple cylindrical shape, and absolutely requires sealability for storing the liquid therein. A left end of the container portion 11 is press fitted in the plug 31, and a right end is closed by a bottom wall 14 integrally formed. The outer container 21 does not require sealability, a slit 25 extending in a longitudinal direction is formed in a side peripheral surface, and a right end surface is not closed and opened in a circular shape. Thus, the outer container 21 entirely has a C-shaped cross section with the slit 25, and is elastically deformed to reduce a space of the slit 25 when the side peripheral surface is pressed by fingers or the like. A ridge 22 extending in the longitudinal direction is formed on an inner peripheral surface of the outer container 21, and a top portion of the ridge 22 comes into contact with the side peripheral surface of the container portion 11. Thus, when the outer container 21 is pressed, the container portion 11 is squeezed to allow the liquid therein to be dropped from the discharge port 12.

As shown in FIG. 1B, the outer container 21 significantly protrudes to the right beyond the bottom wall 14 of the container portion 11. Such a portion protruding rearward beyond the bottom wall 14 of the container portion 11 for storing the liquid is defined as a tail portion 13 in the present invention. The tail portion 13 has no function of storing the liquid, and is a portion intended for easier carrying. The left end surface of the outer container 21 comes into contact with a flange 32 formed on the plug 31, and is integrated with the plug 31 so as not to be removed. Further, a rear pawl 24 is formed at a right end of the ridge 22 on the inner peripheral surface of the outer container 21, and presses the container portion 11 against the plug 31.

Figure 2:
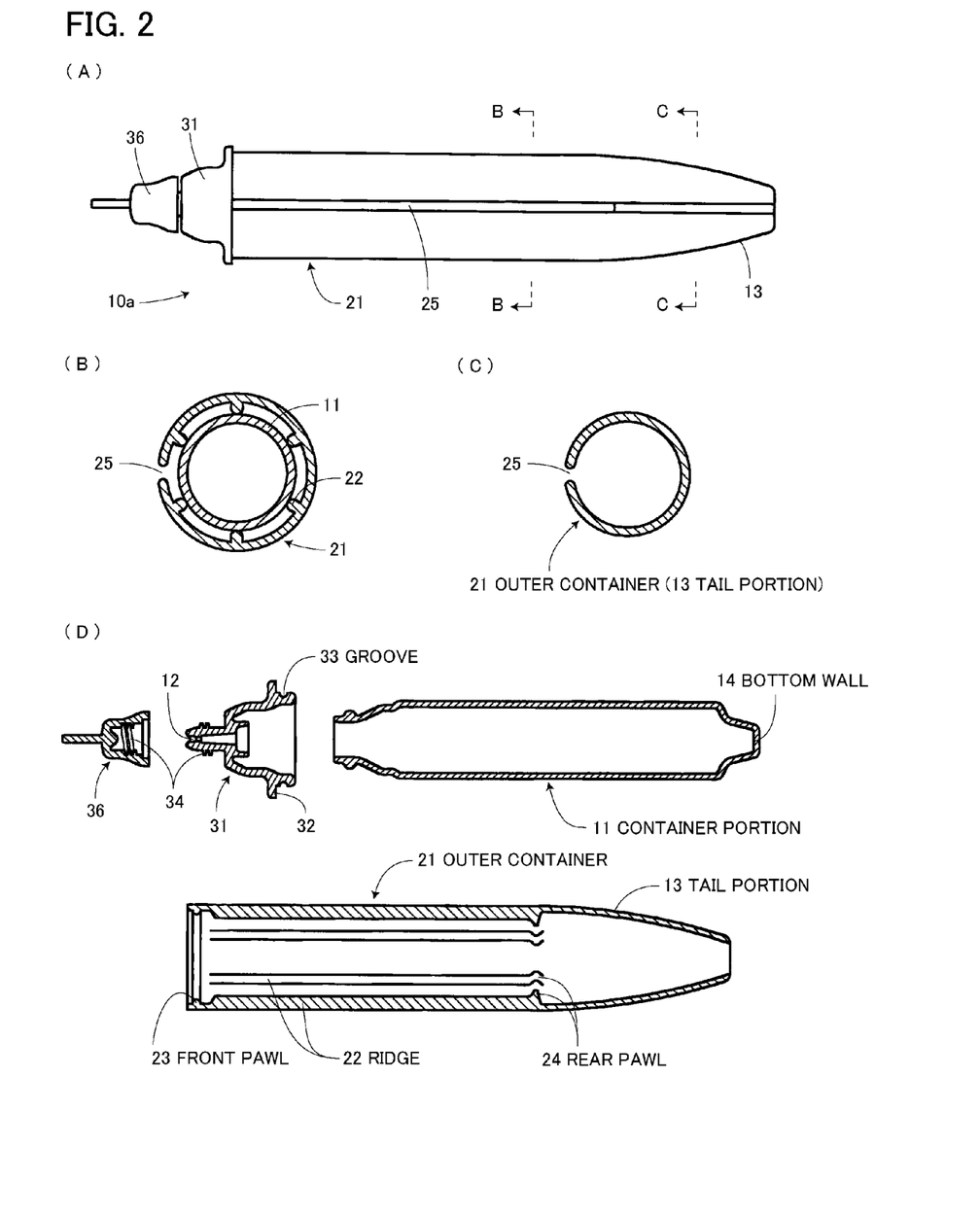
FIG. 2A is a side view.
FIG. 2B is an end view taken along the line B-B in FIG. 2A.
FIG. 2C is an end view taken along the line C-C in FIG. 2A.
FIG. 2D is a vertical sectional view with components being separated.

FIG. 2 shows details of the storage container 10a in FIG. 1, FIG. 2A is a side view, FIG. 2B is an end view taken along the line B-B in FIG. 2A, FIG. 2C is an end view taken along the line C-C in FIG. 2A, and FIG. 2D is a vertical sectional view with components being separated. As shown in FIG. 2A, the storage container 10a according to the present invention has an elongated shape like a pencil, and one line of slit 25 extending in the longitudinal direction is formed in the outer container 21 surrounding the container portion 11. As in the end surface views in FIGS. 2B and 2C, the outer container 21 has a C-shaped section and a total of six lines of ridges 22. The outer container 21 comes into contact with the container portion 11 via the ridges 22, and an air layer is formed in places other than the ridges 22 to ensure a heat insulating property.

Further, as shown in FIG. 2D, the plug 31 and the cap 36 are removable with the threaded portions 34 formed on both thereof. The plug 31 and the outer container 21 are integrated by a groove 33 formed in the outer peripheral surface of the plug 31 meshing with a front pawl 23 formed on the inner peripheral surface of the outer container 21. Further, the rear pawl 24 protruding toward the center is formed at a right end of each ridge 22 on the inner peripheral surface of the outer container 21 for restraining a bottom wall 14 of the container portion 11.

Figure 3:
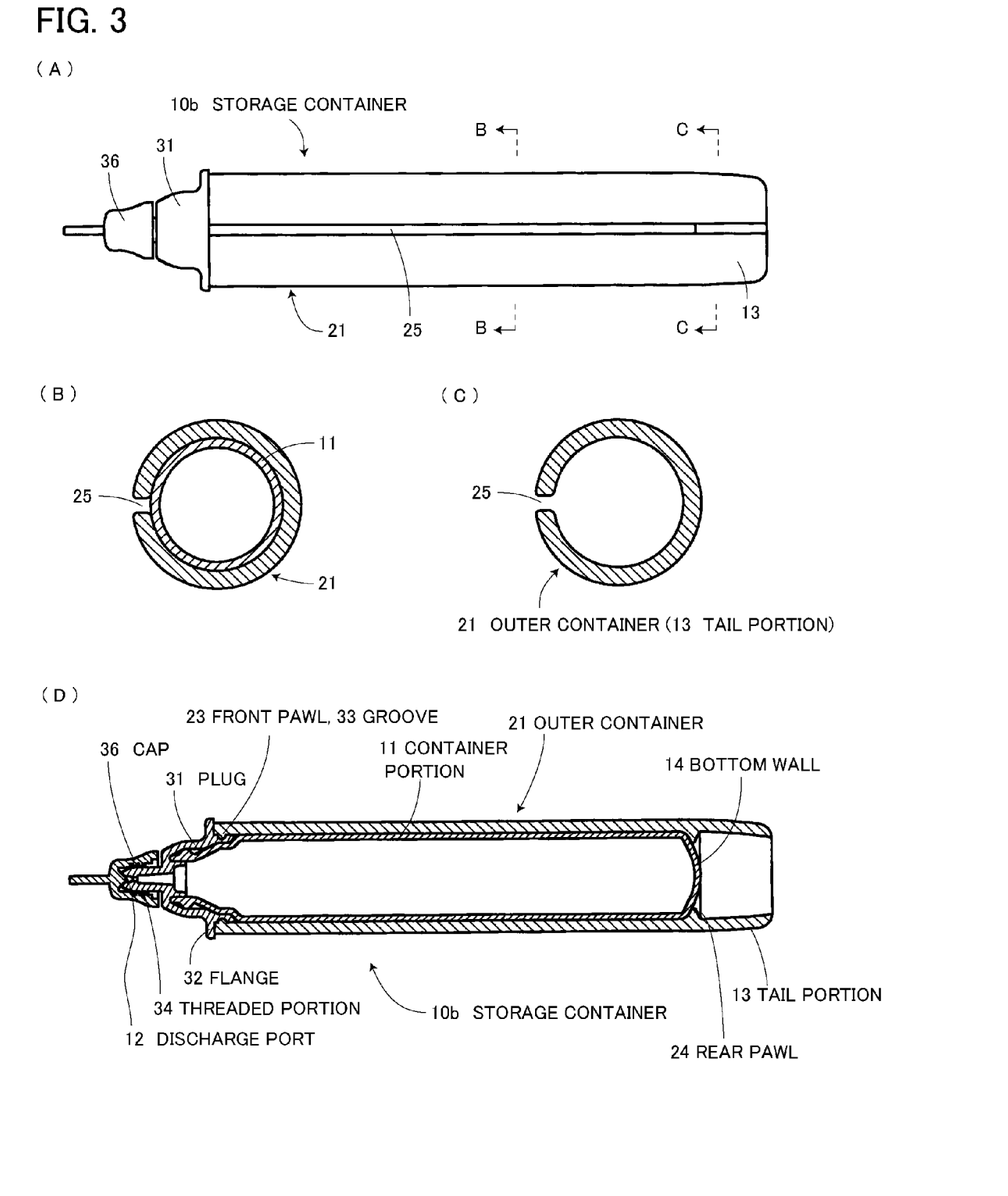
FIG. 3A is a side view.
FIG. 3B is an end view taken along the line B-B in FIG. 3A.
FIG. 3C is an end view taken along the line C-C in FIG. 3A.
FIG. 3D is a vertical sectional view.

FIG. 3 show a storage container 10b having a different structure from the storage container in FIG. 1, FIG. 3A is a side view, FIG. 3B is an end view taken along the line B-B in FIG. 3A, FIG. 3C is an end view taken along the line C-C in FIG. 3A, and FIG. 3D is a vertical sectional view. This structure includes the same container portion 11, plug 31 and cap 36 as in FIG. 1. An outer container 21 has a slit 25, but does not have ridges 22 on an inner peripheral surface thereof, and the entire inner peripheral surface of the outer container 21 except the slit 25 comes into contact with the container portion 11. This can simplify the shape of the outer container 21, and achieve a heat insulating property by ensuring a sufficient thickness of the outer container 21. A tail portion 13 of the outer container 21 in FIG. 3 is shorter than the tail portion 13 in FIG. 1B, but similarly protrudes to the right beyond a bottom wall 14 of the container portion 11. As such, the detailed shape of the outer container 21 may be freely decided on the basis of a size or a material.

Figure 4:
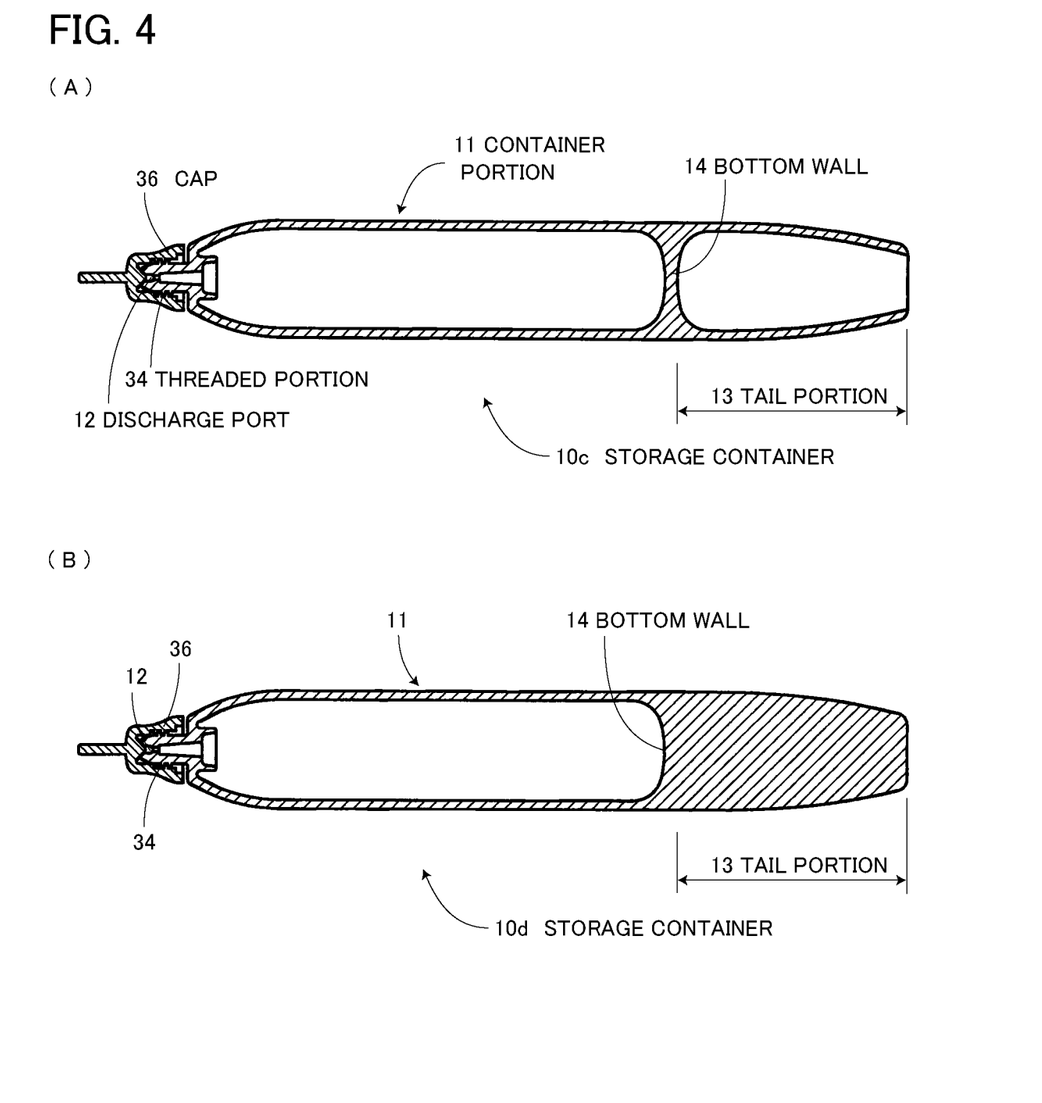

FIG. 4 are vertical sectional views of storage containers 10c and 10d including a container portion 11 and a tail portion 13 integrally formed unlike the storage container in FIG. 1 or the like, FIG. 4A shows a storage container with a hollow tail portion 13, and FIG. 4B shows a storage container with a solid tail portion 13. In the present invention, an outer container 21 is not always necessary as long as the tail portion 13 is formed. Thus, the tail portion 13 may be integrally formed with the container portion 11 for storing a liquid to simplify a structure. With such an integral structure, the tail portion 13 refers to a region rearward of the bottom wall 14 where the liquid cannot be stored, but a simply thickened bottom wall 14 of the container portion 11 is not regarded as a tail portion 13. In FIG. 4, a component corresponding to the plug 31 as in FIG. 1 is not included, and a discharge port 12 is formed at a left end of the container portion 11. As such, the shape around the discharge port 12 can be freely decided without any limitation.

Figure 5:
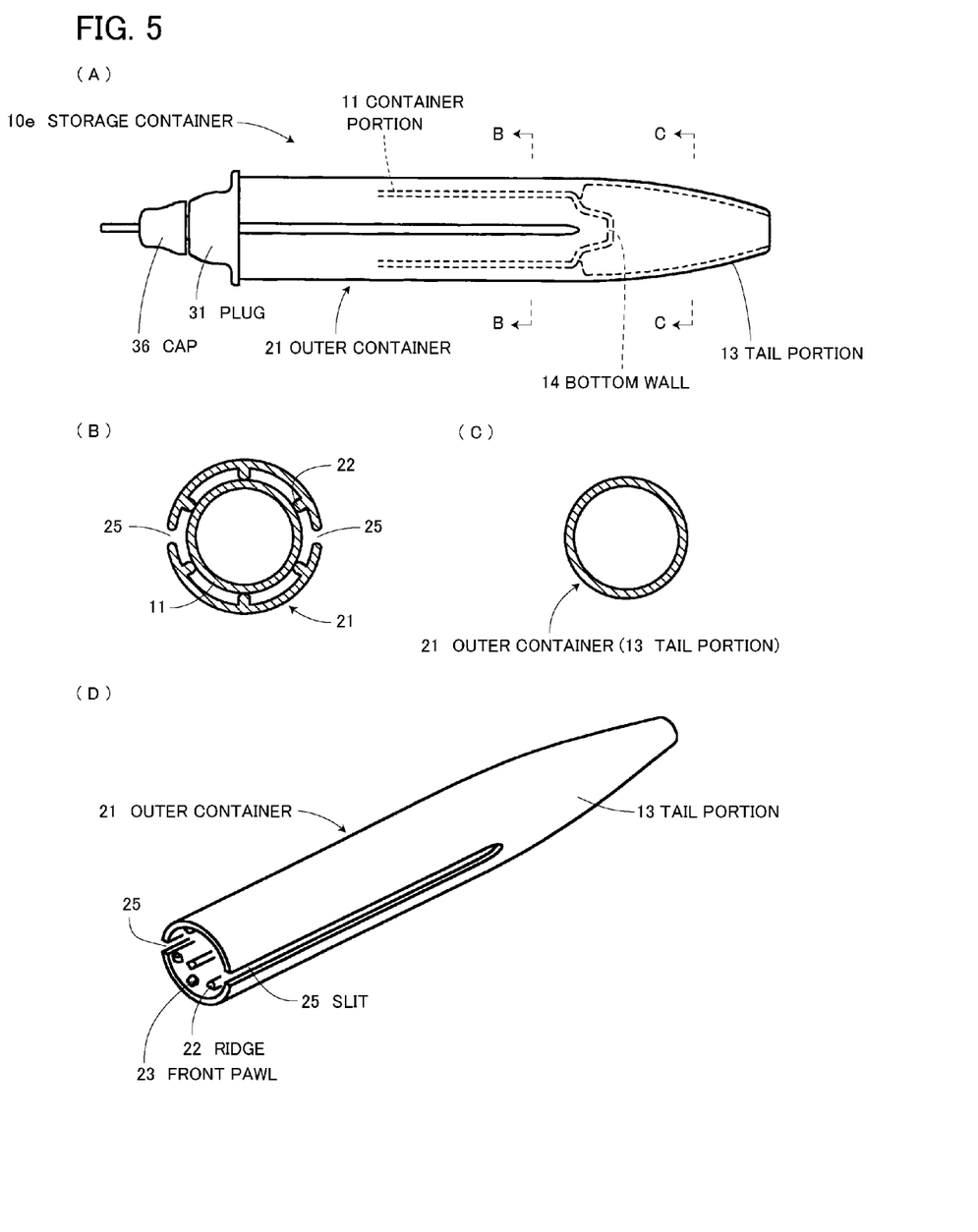
FIG. 5A is a side view.
FIG. 5B is an end view taken along the line B-B in FIG. 5A.
FIG. 5C is an end view taken along the line C-C in FIG. 5A.
FIG. 5D is a perspective view of an outer container only.

FIG. 5 shows a shape example of a further storage container 10e, FIG. 5A is a side view, FIG. 5B is an end view taken along the line B-B in FIG. 5A, FIG. 5C is an end view taken along the line C-C in FIG. 5A, and FIG. 5D shows a shape of an outer container 21 only. This structure also includes the same container portion 11, plug 31, and cap 36 as in FIG. 1. The outer container 21 similarly has a total of six lines of ridges 22 on an inner peripheral surface thereof, but two lines of slits 25 are formed on opposite sides to increase deformability of the outer container 21 and allow more reliable pressing of the container portion 11. Since the two lines of slits 25 are formed, a forming range of the slits 25 is limited so as not to divide the outer container 21.

Figure 6:
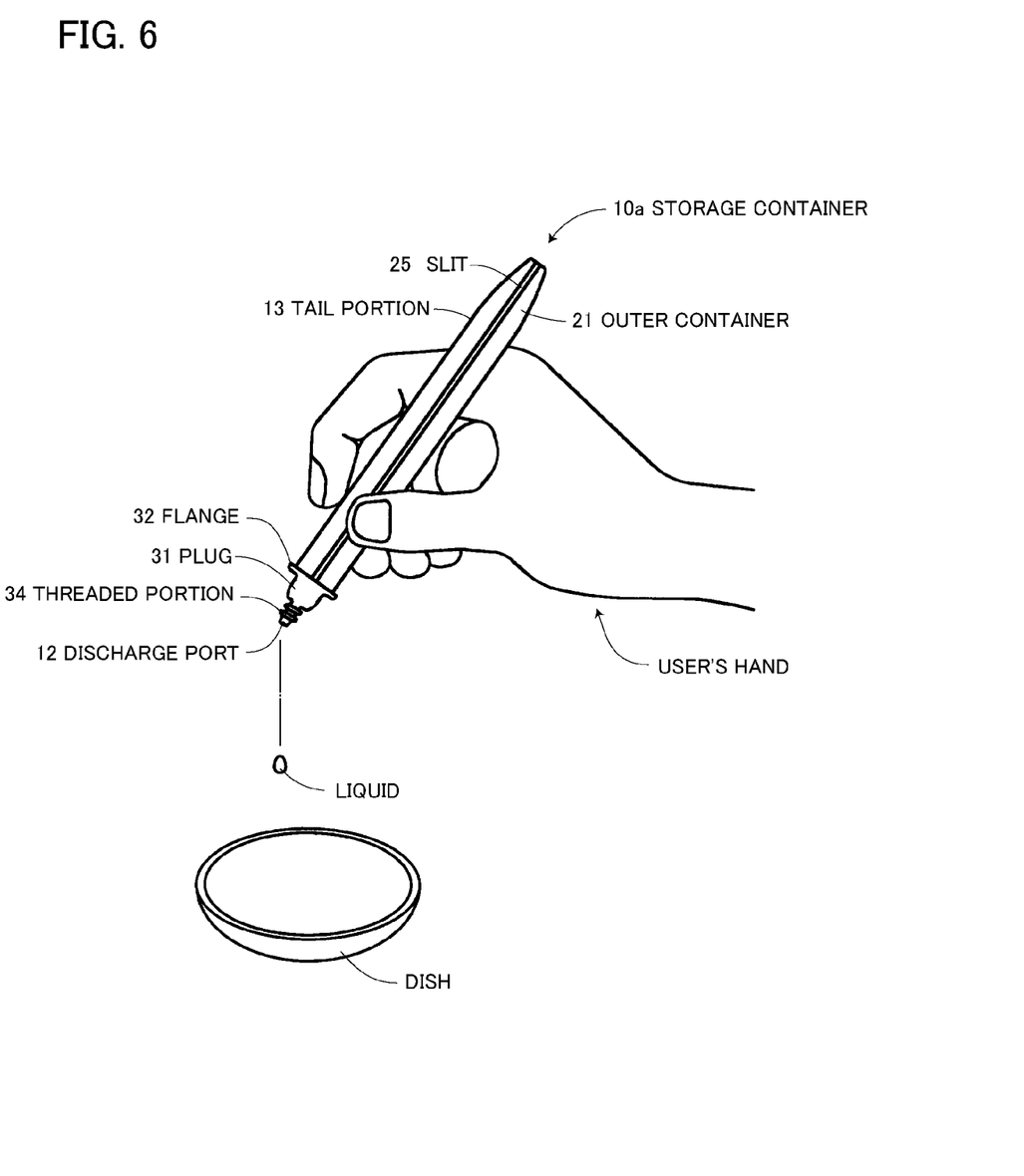
FIG. 6 is a perspective view of a state of use of the storage container according to the present invention.

FIG. 6 shows a state of use of the storage container 10a according to the present invention. As such, the storage container 10a according to the present invention has an appearance like a pencil by a combined use of the tail portion 13. Thus, as shown in FIG. 6, like when a pencil is held, a distal end of the storage container 10a is held by a thumb and an index finger, and then the side peripheral surface is restrained by a middle finger. Further, the tail portion 13 can be supported by a base of the index finger, thereby providing good gripping feeling and allowing handling as desired. Further, the storage container 10a according to the present invention provides high stability of a holding state and a dropping angle during liquid dropping. This also stabilizes a squeeze operation during dropping, thereby allowing a strict desired amount of liquid to be quickly dropped, and preventing a temperature increase caused by heat transfer to the liquid stored in the storage container 10a.

What is claimed is:

1. A storage container for a dental adhesive, comprising an elongated container portion that can store a volatile liquid therein, and an outer container surrounding an outer periphery of said container portion wherein said storage container is comprised of a resin material and a first end surface of said container portion has a discharge port communicating with an outside, a second end surface of said container portion opposite said discharge port first end is sealedly closed by a bottom wall and the outer container portion has a plurality of ridges substantially extending along the length of the longitudinal direction formed on an inner surface of said outer container and come into contact with a side surface of said container portion, forming an air layer between adjacent ridges to ensure a heat insulating property and said storage container is manually squeezed to discharge said liquid therein.

2. The storage container for a dental adhesive according to claim 1, wherein the outer container surrounding an outer periphery of said container portion, has a tail portion formed protruding from said bottom wall to the side opposite from the discharge port and extends in a longitudinal direction of said outer container.

3. The storage container for a dental adhesive according to claim 2, wherein a slit is formed in the longitudinal direction in a side surface of said outer container.

4. The storage container for a dental adhesive according to claim 1, further comprising an outer container surrounding an outer periphery of said container portion.

5. The storage container for a dental adhesive according to claim 4, wherein a slit is formed in the longitudinal direction in a side surface of said outer container.

6. A storage container for a dental adhesive, comprising an elongated container portion that can store a volatile liquid therein, and an outer container surrounding an outer periphery of said container portion, wherein said storage container is comprised of a resin material and a first end surface of said container portion has a discharge port communicating with an outside, a second end surface of said container portion opposite said discharge port first end is sealedly closed by a bottom wall said bottom wall abutting and traversing a pawl on an inner peripheral surface of the outer container near the second end surface of said container, a plurality of ridges extending in the longitudinal direction are formed on an inner surface of said outer container and comes into contact with a side surface of said container portion, an air layer is formed between adjacent ridges to ensure a heat insulating property, and said storage container is manually squeezed to discharge said liquid therein.

7. A storage container for a dental adhesive, comprising an elongated outer container portion that can store a liquid therein, wherein said storage container is comprised of a resin material and a first end surface of said container portion having a discharge port communicating with an outside, a second end surface of said container portion closed by a bottom wall said bottom wall to the side opposite from the discharge port, a tail portion is formed protruding from said bottom wall to the side opposite from the discharge port, a rear pawl formed at the bottom wall end on an inner peripheral surface of the outer container where said bottom wall of storage container extends past the rear pawl into the tail portion and said storage container is manually squeezed to discharge said liquid therein.

8. The invention of claim 7 wherein an inner surface of the outer container has a plurality of ridges extending in the longitudinal direction formed on an inner surface of said outer container and come into contact with a side surface of said container portion, forming an air layer between adjacent ridges to ensure a heat insulating property.

* * * * *